Figure 2:
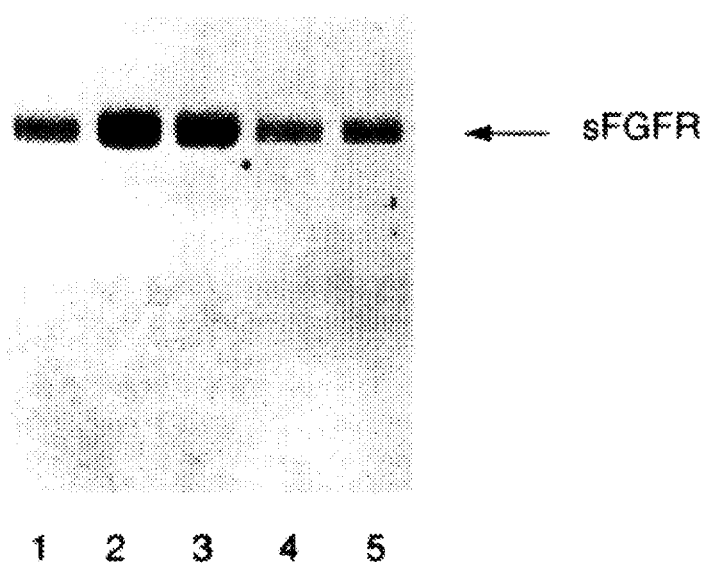

US005783568A

United States Patent [19]
Schlessinger et al.

[11] Patent Number: 5,783,568
[45] Date of Patent: Jul. 21, 1998

[54] METHODS FOR TREATING CANCER AND OTHER CELL PROLIFERATIVE DISEASES

[75] Inventors: Joseph Schlessinger, New York, N.Y.; Irit Lax, Fair Lawn, N.J.; John E. Ladbury, New York, N.Y.; Peng Cho Tang, Moraga, Calif.

[73] Assignees: Sugen, Inc., Redwood City, Calif.; New York University, New York, N.Y.

[21] Appl. No.: 258,307

[22] Filed: Jun. 10, 1994

[51] Int. Cl.$^6$ .................... A61K 31/715; C08B 37/10
[52] U.S. Cl. ................... 514/53; 514/54; 514/56; 514/57; 514/61; 514/2; 514/8; 514/62; 536/21; 536/56; 536/123.1; 536/123.13
[58] Field of Search ................... 514/53, 54, 56, 514/57, 61, 62, 2, 8; 536/21, 56, 123.1, 123.13

[56] References Cited

U.S. PATENT DOCUMENTS

| | | |
|---|---|---|
| 4,021,544 | 5/1977 | Nair et al. ................... 514/54 |
| 5,039,529 | 8/1991 | Bergendahl et al. ................... 424/63 |
| 5,143,829 | 9/1992 | Thompson et al. ................... 435/69.4 |
| 5,164,378 | 11/1992 | Conti et al. ................... 514/56 |
| 5,202,311 | 4/1993 | Folkman et al. ................... 514/12 |
| 5,223,483 | 6/1993 | Thomas et al. ................... 514/12 |
| 5,362,641 | 11/1994 | Fuks et al. ................... 435/209 |
| 5,401,721 | 3/1995 | Folkman et al. ................... 514/12 |
| 5,401,832 | 3/1995 | Linemeyer et al. ................... 530/399 |

FOREIGN PATENT DOCUMENTS

| | | |
|---|---|---|
| 0 245 855 | 11/1987 | European Pat. Off. . |
| 0 331 385 | 9/1989 | European Pat. Off. . |
| 88/05301 | 7/1988 | WIPO . |
| WO 89/05645 | 6/1989 | WIPO . |
| 94/00476 | 1/1994 | WIPO . |
| WO 94/00476 | 1/1994 | WIPO . |

OTHER PUBLICATIONS

Gitay–Goren et al., 1992, "The Binding of Vascular Endothelial Growth Factor to Its Receptors Is Dependent on Cell Surface–associated Heparin–like Molecules", J. Biol. Chem. 267:6093–6098.

Hattori et al., 1990 "Suramin Interrupts Androgen–Inducible Autocrine Loop Involving Heparin Binding Growth Factor in Mouse Mammary Cancer (Shionogi Carcinoma 115) Cells ", Proc. Natl. Acad. Sci. 87:5983–5987.

Kan et al., 1993, "An Essential Heparin–Binding Domain in the Fibroblast Growth Factor Receptor Kinase," Science 259: 1918–1921.

Kasayama et al., 1993, "Suramin Interrupts Androgen–Inducible Autocrine Loop Involving Heparin Binding Growth Factor in Mouse Mammary Cancer (Shionogi Carcinoma 115) Cells, " J. Cell. Phy. 154:254–261.

Klagsbrun et al., 1991, "A Dual Receptor System Is Required For Basic Fibroblast Growth Factor Activity," Cell 67:229–231.

Konturek et al., 1989, "Epidermal Growth Factor in the Gastroprotective and Ulcer–Healing Actions of Sucralfate in Rats," Am. J. Med. 86:32–37.

Konturek et al., 1993, "Fibroblast growth factor in gastroprotection and ulcer healing: interaction with sucralfate," Gut 34:881–887.

La Rocca et al., 1990, "Suramin: Prototype of a New Generation of Antitumor Compounds," Cancer Cells 2:106–115.

Mach et al., 1993, "Nature of the Interaction of Heparin with Acidic Fibroblast Growth Factor," Biochemistry 32:5480–5489.

Schlessinger et al., 1992, "Growth Factor Signaling by Receptor Tyrosine Kinases," Neuron 9:383–391.

Ullrich et al., 1990, "Signal Transduction by Receptors with Tyrosine Kinase Activity," Cell 6:203–212.

Wagner, 1991, "The Fibroblast Growth Factors: An Emerging Family of Neural Growth Factors," Curr. Top. Microbiol. Immunol. 165:95–118.

Wellstein et al., 1991, "Tumor Growth Dependent on Kaposi's Sarcoma–Derived Fibroblast Growth Factor Inhibited by Pentasan Polysulfate," J. Natl. Cancer Inst. 83:716–720.

Yamaguchi et al., 1994, "Differential expression of two fibroblast growth factor–receptor genes is associated with malignant progression in human astrocytomas," Proc. Natl. Acad. Sci. 91:484–488.

Yayon et al., "Cell Surface, Heparin–like Molecules Are Required for Binding of Basic Fibroblast Growth Factor to Its High Affinity Receptor," Cell 64:841–848.

Zhu et al., "1993 Structural studies of the binding of the anti–ulcer drug sucrose octasulfate to acidic fibroblast growth factor," Structure 1:27–34.

Fugedi et al. XVIth International Carbohydrate Symposium, Jul. 5–10, 1992, Paris, France, Abstract No. B113, p. 446.

Fugedi et al. XVIth International Carbohydrate Symposium, Jul. 5–10, 1992, Paris, France, Abstract No. B069, p. 402.

*Primary Examiner*—Kathleen K. Fonda
*Attorney, Agent, or Firm*—Pennie & Edmonds LLP

[57] ABSTRACT

The present invention relates to a method of treating in a mammal certain cancers, other cell proliferative diseases, and/or angiogenesis by using a salt or complex of a sulfated saccharide. The invention also relates to the use of mutant heparin binding growth factors that bind to the growth factor receptor, but not to heparin. The invention also provides pharmaceutical compositions for such methods.

9 Claims, 7 Drawing Sheets

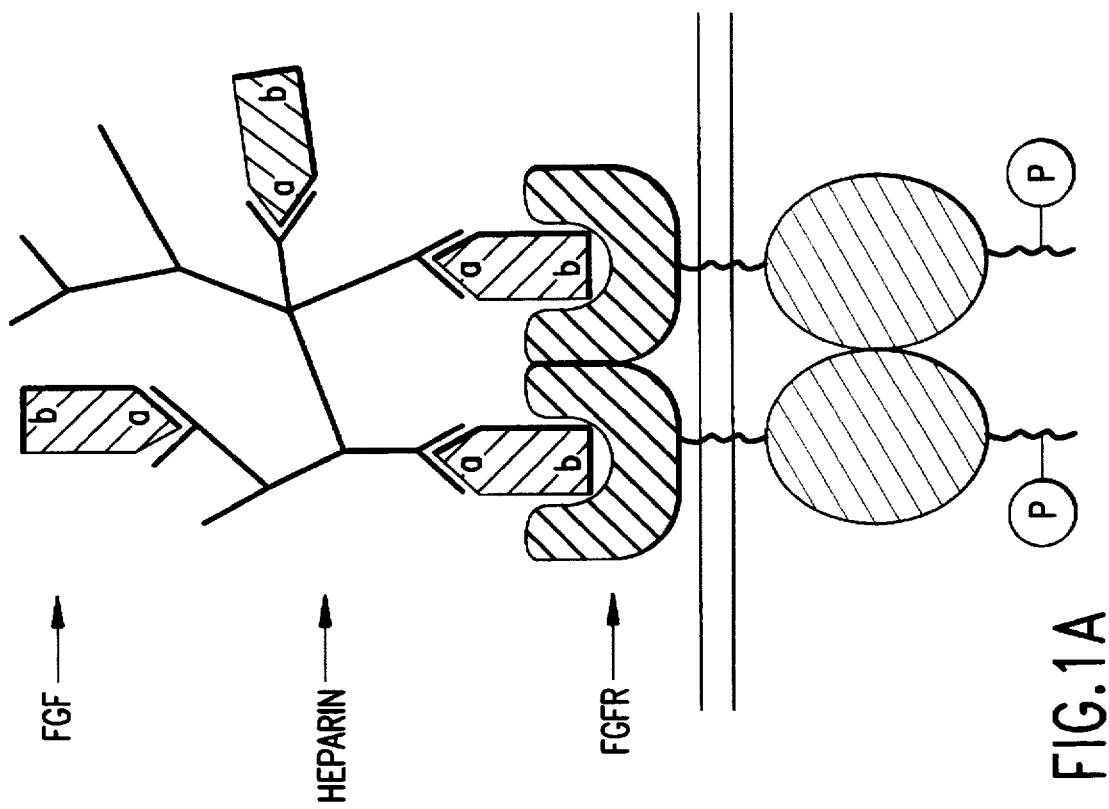
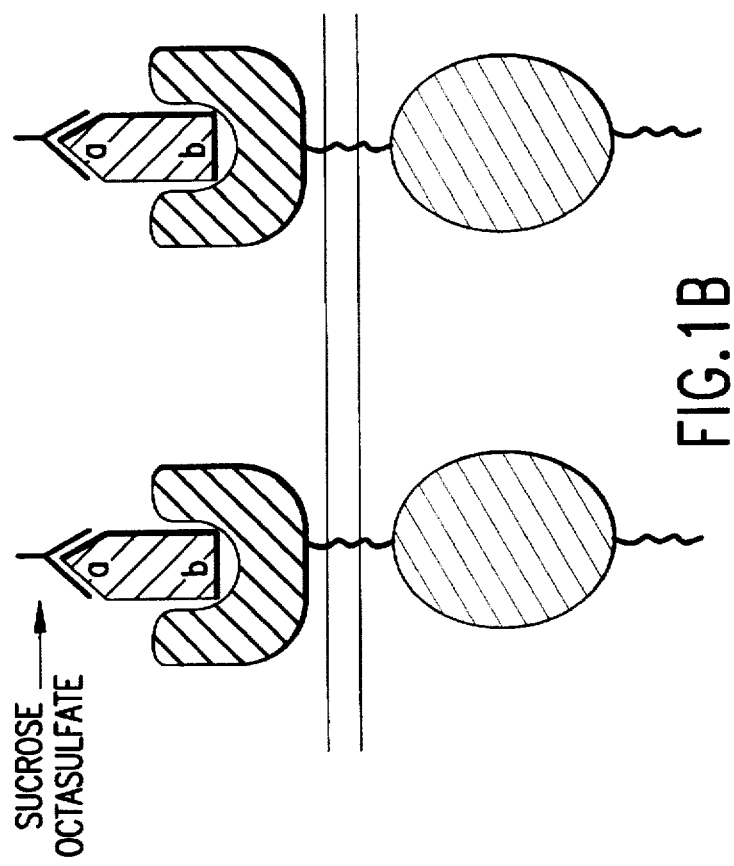
FIG. 1A
FIG. 1B

METHODS FOR TREATING CANCER AND OTHER CELL PROLIFERATIVE DISEASES

1. INTRODUCTION

The present invention relates to a method of treating certain cancers and certain other cell proliferative diseases in mammals using a salt or a complex of a sulfated saccharide. The present invention also relates to a method for regulating or inhibiting heparin-binding growth factor-receptor dimerization or activation. The present invention also relates to a method for inhibiting abnormal angiogenesis induced by heparin-binding growth factors.

2. BACKGROUND OF THE INVENTION

Ligand-induced dimerization is a key event in transmembrane signaling by receptors with tyrosine kinase activity. Receptor dimerization leads to an increase in kinase activity, resulting in autophosphorylation and the induction of diverse biological responses. Reviewed in Schlessinger and Ullrich, 1992, Neuron 9: 383–391. The importance of receptor dimerization for signaling has been illustrated by a number of studies which have shown that co-expression, with wild-type receptors, of receptor mutants that lack a cytoplasmic domain impairs wild-type receptor function. Herskowitz, I., 1987, Nature 329: 219–222. Such a "dominant-negative" effect of defective receptor molecules has been demonstrated not only for tyrosine kinase receptors, Kashles et al., 1991, Mol. Cel. Biol. 10: 4728–4763; Redemann et al., 1992, Mol. Cell. Biol. 12: 491–498; Amaya et al., 1991, Cell 66: 257–270; Ueno et al., 1991, Science 252: 844–847; Ueno et al., 1992, J. Biol. Chem. 267: 1470–1476, but also for receptors from other families. Brakebusch et al., 1992, EMBO J. 11: 943–950.

Certain growth factors, such as platelet-derived growth factor (PDGF); colony stimulating factor-1 (CSF1); and stem-cell factor (SCF), are themselves dimeric proteins, and can induce the dimerization of their respective receptors if each molecule of the dimer binds independently to a separate receptor molecule. Heldin et al., 1988, EMBO J. 7: 1389–1393; Heldin et al., 1989, J. Biol. Chem. 264: 88905–8912; Lev et al., 1992, J. Biol. Chem. 267: 10866–10873. Other growth factors are monomeric, but contain two receptor binding sites, enabling them to cross-link two receptor molecules. A crystal structure of the extracellular domain of the human growth hormone (hGH) receptor in complex with hGH shows that a single molecule of hGH contributes to the stability of the receptor by binding across the dimer interface. de Vos et al., 1992, Science 255: 306–312. The insulin receptor is displayed on the cell surface as a disulfide-linked homodimer, and insulin induces conformational changes in this preexisting receptor dimer. McClain et al., 1987; Schaefer et al., 1992, J. Biol. Chem. 262: 14663–14671. A model for the high-affinity binding of insulin to its receptor has been presented, in which a single molecule of insulin has two receptor-binding sites and interacts simultaneously with both α-subunits of the receptor dimer at distinct sites.

2.1 HEPARIN-BINDING GROWTH FACTORS

Heparin-binding growth factors are a group of proteins characterized by their ability to bind heparin, and which also bind to cell surface protein receptors which are tyrosine kinases. It has been shown that many if not most heparin-binding growth factor receptors require binding of cell surface heparin for activity.

One particular example of heparin-binding growth factors, fibroblast growth factors (FGF), constitute a large family of monomeric growth factors that are important in the control of cell growth, differentiation, and embryogenesis. Wagner, 1991, Curr. Top. Microbiol. Immunol. 165: 95–118; Basilico and Moscatelli, 1992, Adv. Cancer Res. 59: 115–165. Abnormalities in FGF-related signal transduction have been implicated in a variety of cancers including gastric cancer, Hattori et al, 1990, Proc. Natl. Acad. Sci. 87: 5983–5987, brain cancer, Yamaguchi et al, 1994, Proc. Natl. Acad. Sci. 91: 484–488, and Kaposi's sarcoma, Wellstein et al, 1991, J. Natl. Cancer Inst. 83: 716–720. Many FGFs are also powerful angiogenic factors. Klagsbrun et al., 1991, Ann. Rev. Physiol. 53: 217–239. In appropriate angiogenesis contributes to solid tumor growth and disorders such as retinopathies.

FGFs are known to bind to both transmembrane receptors with tyrosine kinase activity, such as FGFR1 (flg) and FGFR2 (bek), and cell surface heparin sulfate proteoglycans. Lee et al., 1989, Science 245: 57–60; Ruta et al., 1989, Proc. Natl. Acad. Sci. USA 86: 8722–8726; Dionne et al., 1990, EMBO J. 9: 2685–2692; Ruoslahti and Yamaguchi, 1991, Cell 64: 867–869. Heparin-like cell-surface molecules are necessary for the induction of a biological response when FGF binds to its high-affinity tyrosine kinase receptor. Rapraeger et al., 1991, Science 252: 1705–1708; Yayon et al., 1991, Cell 64: 841–848; Ornitz et al., 1992, Mol. Cell. Biol. 12: 240–247. A dual receptor model for FGF action has been proposed, in which it is suggested that the low affinity HSPG molecules act to deliver FGF to the high-affinity signaling receptors. Klagsbrun and Baird, 1991, Cell 67: 229–231. Binding of FGF to HSPG may induce a conformational change in FGF that is required for a biologically active interaction with the high-affinity receptor. Since dimerization is a key element of the mechanism of transmembrane signaling by receptors such as FGFR, it has been proposed that this conformational change could involve the induction of FGF oligomerization upon HSPG binding. Ornitz et al., 1992, Mol. Cell. Biol. 12: 240–247.

2.2 DRUGS EMPLOYED TO INHIBIT HEPARIN—BINDING GROWTH FACTOR ACTIVITY

Other heparin-binding growth factors have also been associated with cancer and other disorders. Amphoterin and heparin-binding growth factor-8 are both proteins involved in neurite outgrowth. Merenmies et al, 1991, J. Biol. Chem. 266: 16722–16729; Li et al, 1990, Science 250: 1690–1694. Abnormal activity of these proteins could possibly be involved in various brain cancers. HB17 is a heparin-binding factor expressed in squamous cell and epidermoid carcinomas, Wu et al, 1991, J. Biol. Chem. 266: 16778–16785, and is thus implicated in cell proliferative diseases of the skin.

VEGF is a heparin-binding endothelial cell-specific mitogen that binds to a family of tyrosine kinase receptors expressed in the vasculature. Ferrara and Henzel 1989, Biophys. Res. Commun. 161: 851–858; De Vries et al, 1992, Science 255: 989–991. This growth factor has been implicated as a major regulator of vasculogenesis and angiogenesis both in embryonic development, Millauer et al, 1993, Cell 72: 835–846, and in tumors, Dvorak, H. F., et al, 1991, J. Exp. Med. 174: 1275–1278. Like FGF, binding of VEGF to its receptors is dependent on cell surface-associated heparin-like molecules. Gitay-Goren et al, 1992, J. Biol. Chem. 267: 6093–6098. Kendall and Thomas demonstrated that soluble Flt-1, one of the receptors for VEGF, can bind and inhibit the activity of VEGF in cell culture. Kendall & Thomas, 1993, Proc. Natl. Acad. Sci. 90: 10705–10709. Inhibition of the activation of one of the receptors for VEGF, Flk-1, inhibits tumor growth in vivo, Millauer et al, 1994, Nature 367: 576–579, suggesting that molecules which block the binding/activation of Flk-1 by VEGF would be a useful treatment for cancer.

Suramin, a symmetrical polysulfonated naphthylurea has been found to inhibit a variety of heparin binding proteins by binding to many growth factors and inducing microagglutination of the growth factor. However, the clinical utility of Suramin has been limited due to its narrow therapeutic index. The effect of systemic administration of Suramin to cancer patients has resulted in a series of drug-related side-effects. These include adrenal insufficiency, erythematous rash, vortex keratopathy, coagulopathy and liver function test abnormalities. La Rocca R. V., et al., 1990, J. Clin. Encr. Met. 71: 497–504.

Pentosan polysulfate, a heparin analogue has been used for the development of tumoricidal therapy based on targeting of bFGF. Pentosan polysulfate showed selective inhibition of growth of tumor cells in vitro but its clinical application has been limited because of problems of toxicity. Wellstein et al, 1991, J. Natl. Cancer Inst. 83: 716–720.

Thus, there continues to be a need for new ways of inhibiting heparin-binding growth factor-induced cell proliferation and angiogenesis in cancer and other cell proliferative diseases.

2.3 SULFATED SACCHARIDES AND OTHER HEPARIN-LIKE SUBSTANCES THAT ARE USED TO AUGMENT FGF ACTIVITY FOR TREATING ULCERS AND WOUNDS

Disaccharide polysulfate aluminum compounds have been useful for treating peptic ulcer, conditions of teeth and their supporting tissue, hemorrhoids, wounds and anorectal or dermal wounds. These compounds are believed to interact with and augment FGF Activity.

Basic FGF promotes formation of vascularized granulation tissue, a condition important in wound healing. Basic FGF exists as a naturally occurring peptide in rat and human gastric and duodenal mucosa. In chronic ulcers, the biologic activity of bFGF is rapidly degraded at pH 7.0 or below. Administration of Carafate (sucralfate or aluminum sucrose octasulfate) accelerates ulcer healing without reducing gastric acid. Sucralfate also enhances epithelial proliferation through stimulation of gastric mucosal EGF and PDGF receptors. Konturek et al., 1989, Am. J. Med. 86: 32–37.

The chemical structure of sucralfate, a disaccharide with eight sulfate residues, resembles the repeating disaccharide units of heparin. Sucralfate has higher affinity binding to bFGF than heparin and protects bFGF from degradation by acid. This suggests that sucralfate can act by binding endogenous bFGF, protecting it from acid degradation, and delivering it to the ulcer bed where bFGF induces the ulcer healing. Oral administration of sucralfate elevates the level of available endogenous bFGF in the ulcer bed and stimulates angiogenesis and wound healing. However, bFGF shows little protective activity and is not essential for gastroprotection afforded by sucralfate. Instead, bFGF plays an important part in healing of gastric ulcers possibly due to its growth and angiogenic actions. Konturek et al., 1993, Gut 34: 881–887.

Sulcralfate binds EGF in a pH-dependent manner and to accumulate it in ulcer areas. The EGF is available locally in high concentrations to accelerate tissue repair and the healing process in ulcerated mucosa. EGF is not essential for the gastroprotection induced by sucralfate, but seems to play an important role in the ulcer-healing action of this drug. Konturek, 1989, Am J. Med. 86: 32–37.

A related disaccharide sulfated agent, sucrose octasulfate (SOS) has also been shown to protect the biologic activity of bFGF against acid degradation. One mechanism proposed from these observations is that SOS protects bFGF from degradation. These observations suggest that SOS may preserve or even enhance the mitogenic and angiogenic activities of BFGF.

3. SUMMARY OF THE INVENTION

The present invention relates to a method of treating in a mammal certain cancers, other cell proliferative diseases, and/or angiogenesis by using a salt or complex of a sulfated saccharide. The invention also relates to the use of mutant heparin binding growth factors that bind to the growth factor receptor, but not to heparin. The invention also provides pharmaceutical compositions for such methods.

The invention is based, in part, on the discovery that (a) heparin causes oligomerization of the FGF ligand such that binding of the oligomerized ligand to its receptor results in dimerization and consequent activation of the receptors and (b) synthetic compounds that interact with heparin-binding site and that bind to FGF ligand in a monovalent manner can block FGF-receptor dimerization and activation.

The invention is illustrated by working examples which characterize the interaction of aFGF with FGFR2 (bek), as well as the requirement for heparin-like molecules in ligand-binding and receptor activation. The in vitro studies of aFGF binding to the purified soluble extracellular-ligand binding domain of FGFR2 (sFGFR) indicate that heparin is not required for the ligand/receptor interaction. aFGF binds to sFGFR with a 1:1 stoichiometry ($K_D$=528 nM), and the addition of heparin does not detectably affect the interaction. Binding of aFGF alone to sFGFR did not, however, result in the formation of dimers of the receptor extracellular domain, as has been observed for EGF binding to a soluble form of its receptor. Lax et al., 1991, J. Biol. Chem. 266: 13823–13833; Hurwitz et al., 1991, J. Biol. Chem. 266: 22035–22043. In the presence of heparin, however, the binding of aFGF to sFGFR did lead to its dimerization. Binding of heparin itself to sFGFR could not be detected. However, a single 16 kDa heparin molecule can bind up to 11 molecules of aFGF ($K_D$=461 nM). Heparin thus induces the oligomerization of aFGF molecules, which is demonstrable using chemical cross-linking techniques. The working examples further show that this oligomerization allows aFGF to induce receptor dimerization, via multivalent binding of the aFGF/heparin complex to individual sFGFR molecules. The heparin requirement for FGF-induced receptor dimerization is also evident when FGF receptors are expressed in mutant CHO cells that are deficient in heparin sulfate. The data presented herein support the conclusion that dimerization of the soluble receptor in vitro and the full-length receptor in vivo requires the concerted action of both FGF and heparin molecules, and that aFGF-induced receptor dimerization is mediated by heparin stabilized oligomers of aFGF molecules. Moreover, compounds that block the interaction between FGF and heparin prevent dimerization and subsequent activation of the receptor.

4. BRIEF DESCRIPTION OF THE DRAWINGS

FIG. 1. Heparin-Induced Oligomerization of aFGF is responsible for FGFR dimerization and activation.

FIG. 1A. A schematic representation of the model suggested by the data presented here for the action of heparin as an accessory molecule in aFGF-induced activation of FGFR. Heparin binds to a number of aFGF molecules, resulting in their oligomerization. The independent, monovalent, binding of several of these aFGF molecules to FGFR then results in oligomerization and activation of the receptor.

FIG. 1B. A schematic representation of the manner in which sucrose octasulfate could act as an antagonist to heparin's action as an accessory molecule. Sucrose octasulfate binds to only a single aFGF molecule, and therefore cannot induce its oligomerization. The aFGF/sucrose octasulfate complex is not able to induce FGFR dimerization.

FIG. 2. Purified soluble extracellular domain of FGFR (sFGFR).

sFGFR was purified from either CHO or Sf9 cells conditioned media as described in Materials and Methods. Shown in the figure are fractions (1–5) eluted at the final step of purification from a lectin affinity column. These fractions were analyzed by 15% SDS-PAGE and stained with Coomassie blue.

Figure 3:
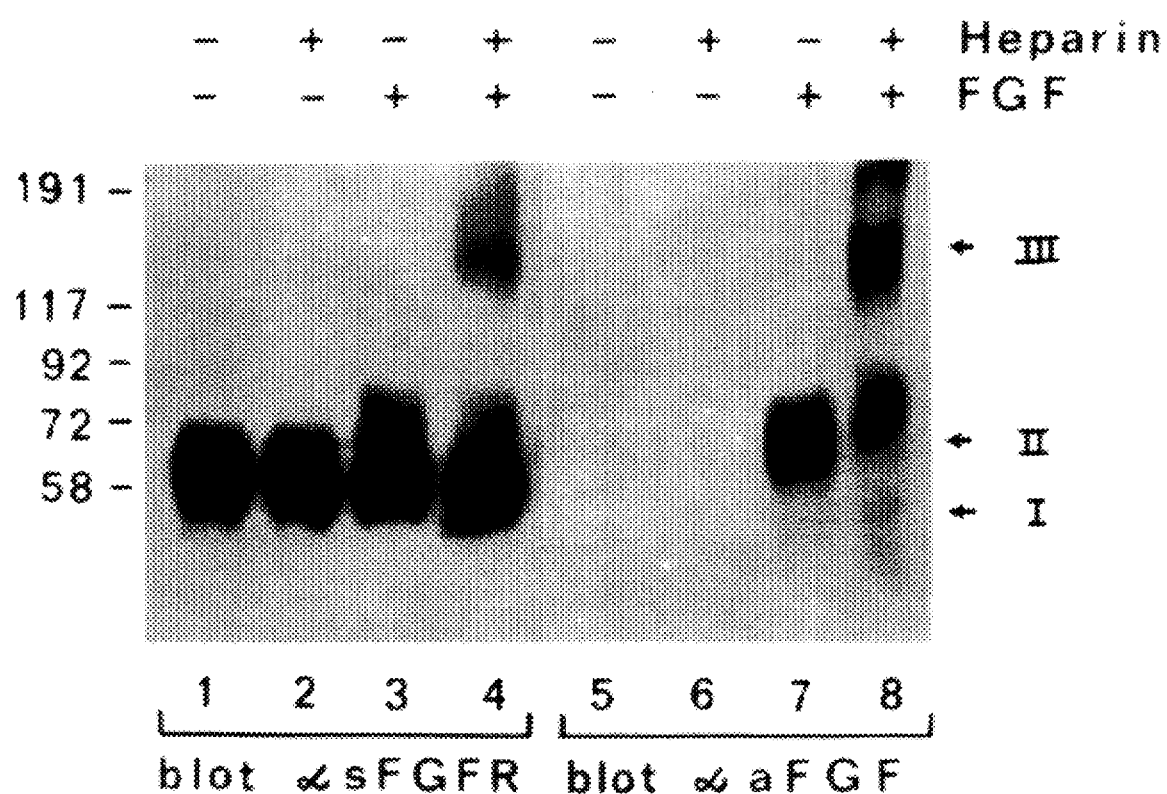

FIG. 3. aFGF Induces sFGFR Dimerization only in the Presence of Heparin.

Purified sFGFR was incubated with aFGF in the presence (lanes 2, 4, 6 and 8) or absence (lanes 1, 3, 5 and 7) of heparin for 1 hour at room temperature. The covalent cross-linker, DSS, was then added and incubation was continued for a further 45 minutes. Samples were then boiled in Laemmli sample buffer, separated by SDS-PAGE (6–12% gradient gel), and transferred to a nitro-cellulose membrane. The protein bands were visualized by blotting with anti-FGFR2 (lanes 1–4) or anti-aFGF antibodies (lanes 5–8), followed by $^{125}$I-protein A. I-sFGFR monomers; II-aFGF/sFGFR complex (monomeric); III-aFGF/sFGFR complex (dimeric).

Figure 4A:
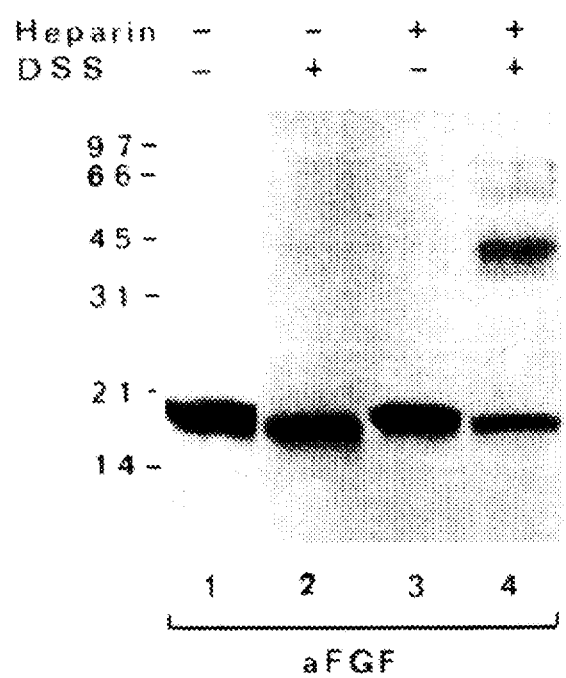
Figure 4B:
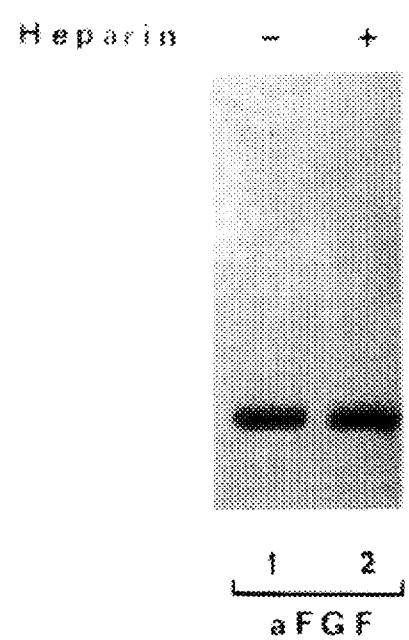

FIGS. 4A and 4B. Heparin Induces FGF oligomerization.

aFGF was incubated with or without heparin, in the presence (A) or absence (B) of cross-linker (DSS) for 45 minutes at room temperature. The samples were then separated by SDS-PAGE (15% acrylamide) under either reducing (A) or non-reducing (B) conditions. Protein bands were visualized by staining with Coomassie blue. Molecular weight markers are in given in kDa.

Figure 5:
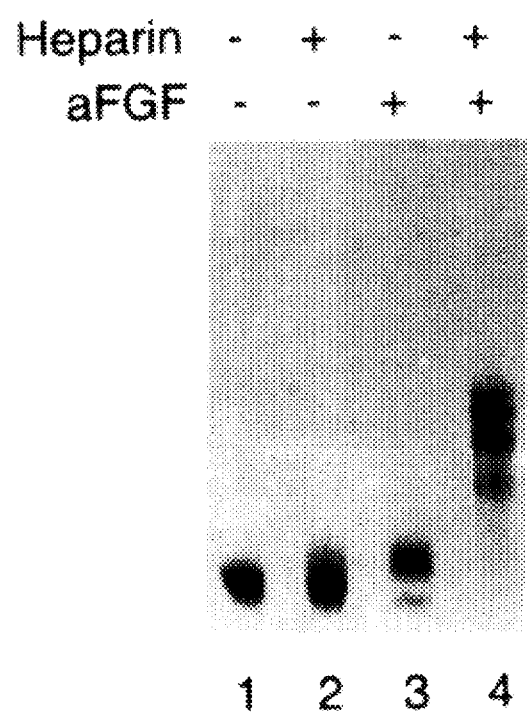

FIG. 5. Analysis of sFGFR/aFGF/heparin complex formation by non-denaturing PAGE.

aFGF, heparin or a mixture of aFGF and heparin were added to sFGFR. Free aFGF and sFGFR were separated from the complexes by gel-filtration, and fractions containing the complexes were analyzed by non-denaturing PAGE. Proteins were visualized by staining with Coomasie Brilliant blue. Various oligomerization states of aFGF/sFGFR are detected only in the presence of heparin.

Figure 6:
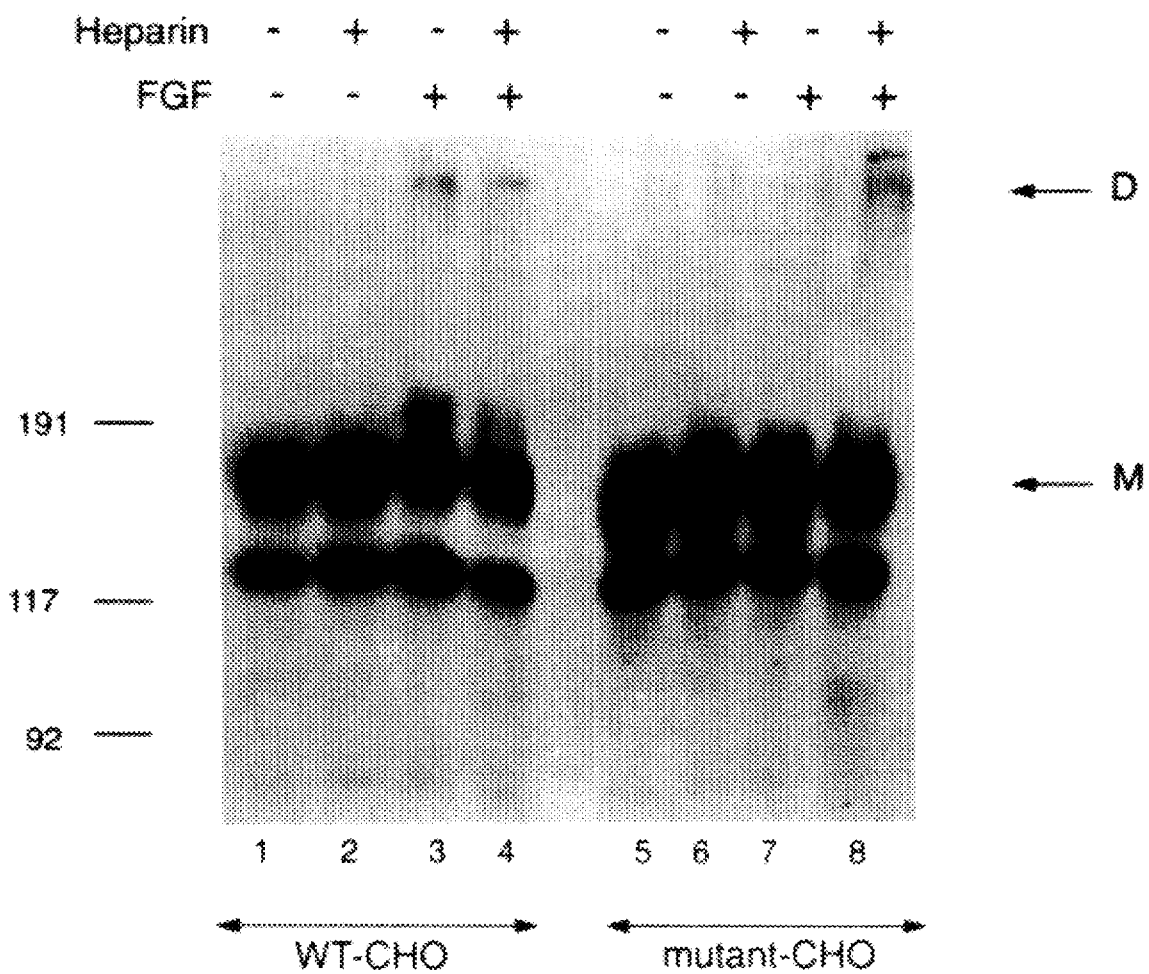

FIG. 6. Heparin is required for FGF-induced dimerization in CHO cells.

Parental (lanes 1–4) and mutant CHO cells (lanes 5–8) were incubated with either 50 nM heparin (lanes 2 and 6), 0.1 nM aFGF (lanes 3 and 7), or both (lanes 4 and 8), for 1 hour at 4° C. Cells were then treated with the covalent cross-linking agent BS$^3$ for 30 min at room temperature, solubilized and immunoprecipitated with anti-FGFR2 antibodies. The samples were analyzed by a gradient SDS gel (6–8%), transferred to nitrocellulose membranes and probed with anti-FGFR2 antibodies. M—FGFR monomers; D—FGFR dimers.

Figure 7:
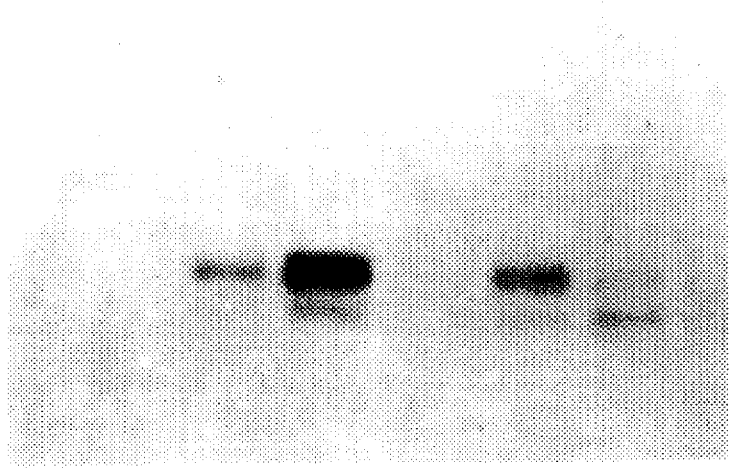

FIG. 7. aFGF-induced autophosphorylation of FGFR expressed in CHO cells requires heparin, and can be inhibited by the monovalent heparin analog, sucrose octasulfate.

CHO-K1 parental cells (WT-CHO), and CHO-pgsD-677, HSPG-deficient clones (mutant-CHO), were incubated with the indicated combinations of 50 nM heparin and 0.1 nM aFGF, plus (where indicated) 0.5, 50 or 500 µM sucrose octasulfate, for 5 minutes at 37° C. Cells were lysed and the receptor was immunoprecipitated with anti-FGFR2 antibodies. Samples were then analyzed by SDS-PAGE, transferred to nitrocellulose membranes, and tyrosine-phosphorylated proteins were detected by immunoblotting with anti-phosphotyrosine antibodies.

5. DETAILED DESCRIPTION OF THE INVENTION

The present invention relates to pharmaceutical compositions and methods for treating certain cancers, other cell proliferative diseases, and/or angiogenesis in mammals, including humans, by administering to a mammal in need of said treatment a therapeutically effective amount of a salt or complex of a sulfated saccharide.

The sulfated saccharide compounds of the invention bind the heparin-binding growth factors-ligands in a monovalent manner and prevent or disrupt the formation of the heparin stabilized ligand:receptor complexes required for dimerization and activation of the receptor involved in the condition treated. Thus, the sulfated compounds inhibit cancer or cell proliferative diseases by inhibiting the activity of heparin-binding growth factors.

The invention also relates to the use of mutant heparin binding growth factors that bind to the growth factor receptor, but not to heparin.

The various aspects of the invention are described in more detail in the sections that follow.

5.1. THE ROLE OF HEPARIN IN RECEPTOR ACTIVATION

While it is known that a variety of growth factors associate with heparin, this interaction has been most widely studied using FGFs. The results presented herein indicate a novel mechanism via which binding of a growth factor to its cognate receptor leads to dimerization and activation of the receptor. In a well defined in vitro system described in Section 7.2.4, infra, the soluble extracellular portion of FGFR2 (sFGFR) was induced to form dimers upon aFGF binding, but only in the presence of heparin. Heparin does not influence the affinity of the aFGF/sFGFR interaction, and does not itself interact with sFGFR. Rather, it binds to aFGF in a multivalent manner, and induces its oligomerization. The resultant aFGF/heparin complex can then bind to a number of sFGFR molecules, with individual aFGF molecules in the complex participating in the 1:1 aFGF/sFGFR interaction shown by our studies. This results in the oligomerization of sFGFR.

Studies of the full-length receptor in mutant cells that express little or no HSPG at their cell surface gave identical results with respect to the influence of heparin upon aFGF-induced receptor oligomerization. (See Section 7.2.7, infra.) In these studies, the influence of heparin upon aFGF-induced receptor activation was shown to be identical. In the wild-type cell-lines that do express HSPG at their surfaces, these heparin-like molecules achieve the same effect as exogenously added heparin. The multimeric, heparin-bound, aFGF has a higher affinity for the full-length cell surface receptor than does free monomeric aFGF. The foregoing results support a model for the manner in which heparin-like molecules function in vivo as accessory molecules for heparin-binding growth factor, and FGF in particular, stimulation of its receptors. This model is depicted in FIG. 1A, which shows how heparin-induced oligomers of aFGF could induce dimerization of FGFR.

Heparin analogs that bind monovalently to heparin-binding growth factors are effective antagonists. The data described herein shows that one such analog, sucrose octasulfate, which forms a 1:1 complex with aFGF, effectively inhibits aFGF/heparin-induced dimerization and activation of FGFR. (See Section 7.2.8, infra.) The synthesis of and treatment with such analogs therefore provides a novel avenue for pharmacological intervention in cases where the action of heparin-binding growth factors is associated with an abnormal condition such as cancer. Furthermore, highly specific antagonists may be developed in which the heparin binding sites in these growth factors have been identified and eliminated by site directed mutagenesis. Mutants may also be deletion mutants in which the entire or a significant portion of the heparin-binding site is deleted from the protein. The mutants of the invention will retain the ability to bind to receptors but not have the ability to bind heparin-like molecules.

5.2. THE SULFATED SACCHARIDES OF THE PRESENT INVENTION

The saccharide component of the sulfated saccharide used in accordance with the invention is a monosaccharide, for example, xylose, fructose or glucose, an oligosaccharide, for example, a disaccharide such as sucrose, lactose, maltose or cellobiose, or maltotriose, maltotetrose, maltopeptose, maltohexose, or fragments of heparin small enough not to bind more than one heparin-binding growth factor at a time or a subunit of any of such saccharides.

The saccharide is sulfated, i.e., $SO_3$, and is preferably polysulfated which means that two or more sulfate-containing moieties are present as substituents on the saccharide, or persulfated which means that all possible sites on the molecule are sulfated.

The sulfated saccharide of the present invention is in the form of a salt with for example, a metal, e.g., an alkali or alkaline earth metal such as Na, K, Ca, Sr, Mg, or Ba, or Al, Zn, Cu, Ga, Bi and Mn, or in the form of a complex with an organic base. The salts are preferably selected from those salts which are soluble in water, in order to obtain a fast release effect when they are administered to a mammal.

A preferred class of sulfated saccharides is potassium disaccharide polysulfate of which the most preferred substance is potassium sucrose octasulfate.

Sucrose octasulfate is represented by the following formula:

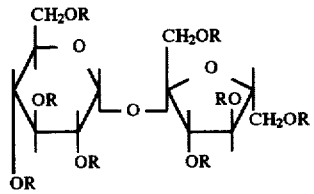

Another preferred metal is aluminum, optionally in the form of aluminum hydroxide. A preferred class of sulfated saccharides is aluminum disaccharide polysulfate of which the most preferred is sucralfate.

Sucralfate is represented by the following formula:

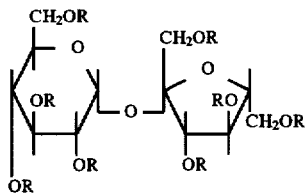

$R = SO_3 Al(OH)_2$.

Sucralfate can be termed sucrose octakis (hydrogen sulfate) aluminum complex. The substance can, for example, be prepared as disclosed in U.S. Pat. No. 3,432,489.

In some cases, the sulfated saccharide is a cyclic moiety, e.g., persulfated cyclodextrin as represented by the following formula:

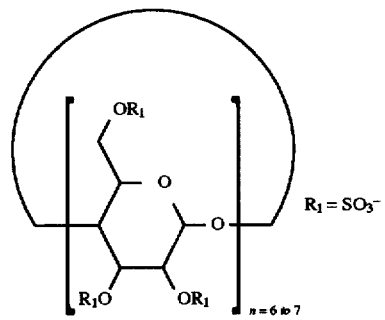

Persulfated Cyclodextrin

In some cases the sulfated compound is a negatively charged Calix like compound represented by the following formula:

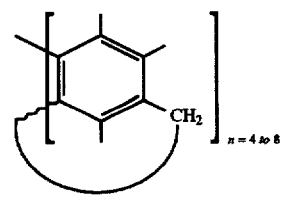

Calix Sulfatoid

Substituted with one to two $OSO_3^-$ or $SO_3^-$

In some cases the sulfated saccharide is made of hexasaccharide units having an anomeric linkage as represented by the following formulae:

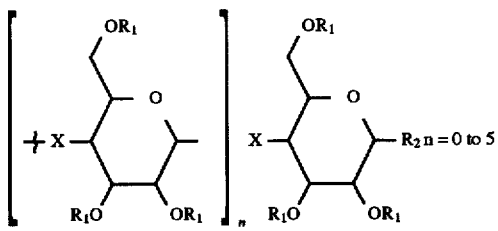

$X=O$ when n is greater than 1, or $X=OSO3^-$ when $n=0$ or the sugar unit is at the non-reducing end.

$X = OSO_3^-$ $R_2 = H, OH, CH_2OH, CH_2OSO_3^-, OSO_3^-, OR_4$ where $R_4$ is C1 to C12 substituted or non substituted alkyl, aryl or alkyl aryl (C1–C12)

$R_2 = $ aryl $R_2 = C1$ to C20 substituted or non substituted alkyl, alkyl aryl (C1–C12)

$R_2 = OCH[CHOSO3^- (CH2OSO3^-)] (CHOSO3)_2 CH2OSO3^-$ $R_2 = CH2(CHOSO3^-)mCH2OSO3^-$ M=3 to 4 C-glycoside.

$R_2 = $ When n=0 or 1, 2 to 6 amino acid peptide chosen from the available natural and unnatural amino acids preferably from serine, threonine, aspartic acid, and glutamic acid which are optionally sulfated. The linkage can be O-, C- or N-linked.

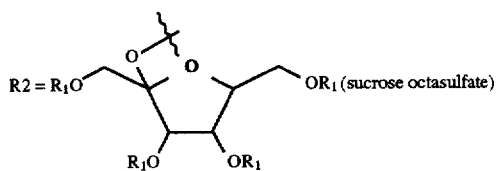

$R_2 = OCH(CHOSO3^-)p(CH_2)q$ p=3 to 4; q=0 to 2; and p+q>4

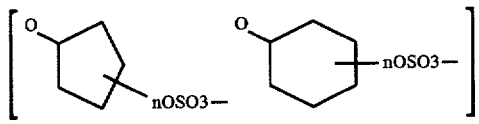

$R_2 = NR_5COR_5$ WHERE $R_5$ IS $C_1$ to $C_{12}$ alkyl

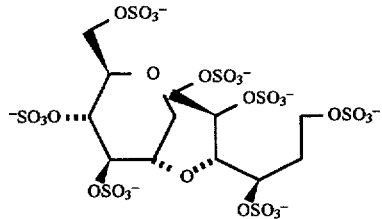

$R_2 = $ Maltose

In other cases the sulfated compound is an analog of sucrose of the following formula:

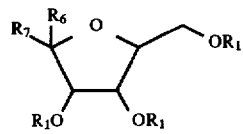

$R_6 = OCH2(CHOSO3^-)mCH2OSO3^-$ m=3 to 4
$R_6 = CH2(CHOSO3-)mCH2OSO3-$ M=3 to 4

$OCH(CHOSO3^-)p(CH2)q$ p=3 to 4 and q=0 to 2; p+q>4
$R_6 = $ when n=0 or 1, 2 to 6 amino acid peptides chosen from the available natural and unnatural amino acids preferably from serine, threonine, aspartic acid, glutamic acid which are optionally sulfated. The linkage can be O-, C- or N-linked.

5.3 HEPARIN-BINDING GROWTH FACTOR ANTAGONISTS

The invention also relates to the use of mutant heparin-binding growth factors that bind to the heparin-binding growth factor receptor but do not bind heparin. Using the site-directed mutagenesis technique to introduce mutations at predetermined sites, specific mutants that selectively bind to the heparin-binding growth factor receptor but not to heparin, can be produced. Site-directed mutagenesis techniques which are well known in the art may be used and are described in detail in Molecular Cloning, A Laboratory Manual, Cold Spring Harbor Laboratory, N.Y., 1989, ed. J. Sambrook, E. F. Fritsch and T. Maniatis, Sec. 15.

The mutant thus produced can then be expressed in an appropriate host-cell/vector system. A variety of host-expression vector systems may be utilized to express the mutant coding sequences. Such host-expression systems represent vehicles by which the coding sequences of interest may be expressed and subsequently purified, but also represent cells which may express the mutant molecule in situ. Methods of construction of such vectors and use of such host cells are well known. See Sambrook et al., 1989.

By comparing the properties of the mutant molecules and the various wild-type forms of heparin-binding growth factors, mutants that bind to heparin-binding growth factor receptors but not bind to heparin can be identified and isolated. Yayon et al., 1991, Cell 64: 841–848; Schlessinger and Ullrich, 1991, Neuron 9: 383–391; and Klagsbrun and Baird, 1991, Cell 67: 229–231.

The mutant molecules identified in the above tests, may be further evaluated for their ability to antagonize the biological activity of unmutated heparin-binding growth factors in cell-based assays, e.g., cell lines that express the receptor and/or in vivo in animal models. The ability of a mutant growth factor to interfere with binding of the unmutated ligand and/or receptor signal transduction may be measured by standard biochemical techniques and/or assaying cellular responses; e.g., by assaying activation or suppression of catalytic activity, phosphorylation or dephosphorylation of other proteins, activation or modulation of second messenger production, changes in cellular ion levels, association, dissociation or translocation of signalling molecules, or transcription or translation of specific genes may be monitored. These assays may be performed using conventional techniques developed for these purposes. E.g., see Rapraeger et al., 1991, Science 252: 1705–1708; Yayon et al., 1991, Cell 64: 841–848; Ornitz et al., 1992, Mol. Cell. Biol. 12: 240–247; Kendall & Thomas, 1993, Proc. Natl. Acad. Sci. 90: 10705–10709. After this screening procedure, the antagonist mutants may be purified and used in vivo.

5.4. PHARMACEUTICAL FORMULATIONS, DOSAGES AND MODES OF ADMINISTRATION

The particular compounds that affect the activity of heparin-binding growth factors and the disorders of cancer or other cell proliferative diseases of interest can be administered to a patient either by themselves, or in pharmaceutical compositions where it is mixed with suitable carriers or excipient(s).

In treating a patient exhibiting cancer or a cell proliferative disorder of interest, a therapeutically effective amount of an agent or agents such as these is administered. A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal disruption of the heparin-binding growth factor receptor (HBGF) dimerization, or a half-maximal inhibition of the cellular level and/or activity of HBGF receptors) as determined in cell culture. Such information can be used to more accurately determine useful doses in humans. Levels in plasma may be measured, for example, by high performance liquid chromatography (HPLC).

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the clinical disorder of interest will vary with the severity of the condition to be treated and the route of administration. The severity of the condition may, for example, be evaluated, in part, by appropriate prognostic evaluation methods. Further, the dose and perhaps dose frequency, will also vary according to the age, body weight, and response of the individual patient. A program comparable to that discussed above may be used in veterinary medicine.

Depending on the specific conditions being treated, agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For example pharmaceutical preparations of sucralfate are currently available in the solid form such as tablets, granules, pellets or powder. Sucralfate is also available as an aqueous suspension, a solution, salve, paste, gel, cream, dental fixative, periodontal implant, chewing gum, chewable tablet, effervescent tablet or lozenge. U.S. Pat. No. 5,240,710.

5.5 USES OF THE DISCLOSED COMPOUNDS

The compounds and methods disclosed herein can be used to treat a variety of diseases or conditions, notably those that are characterized by abnormal or inappropriate activity of a heparin-binding growth factor and/or its receptor. Inappropriate activity of a heparin-binding growth factor and/or its receptor can be, for example, the result of over production of ligand, abnormal production of ligand (either by being produced by cells that would not produce the ligand normally or at an abnormal time), overexpression of the receptor or otherwise abnormal receptor activity.

By "disease or condition" it is meant a state in an organism which is recognized as abnormal by members of the medical community. Examples of disease or conditions to be treated by the present invention include cell proliferative diseases such as cancers and abnormal or inappropriate angiogenesis. Angiogenesis, the growth of new blood capillary vessels, is required for a number of physiological processes ranging from wound healing, tissue and organ regeneration, placental formation after pregnancy and embryonic development. Abnormal proliferation of blood vessels is an important component of a variety of diseases such as rheumatoid arthritis, retinopathies, and psoriasis. Angiogenesis is also an important factor in the growth and metastatic activity of solid tumors that rely on vascularization. Therefore, inhibitors of angiogenesis may be used therapeutically for the treatment of diseases resulting from or accompanied by abnormal growth of blood vessels and for treatments of malignancies involving growth and spread of solid tumors.

5.5.1 TREATMENT OF FGF-SENSITIVE DISORDERS

The compounds and method of the invention can be used to treat a number of abnormalities in the FGF family signal transduction pathways implicated in a variety of tumors, including, but not limited to those described below.

Differential expression of two FGF-receptor genes is associated with malignant progression in human intracranial tumors such as astrocytomas. The malignant astrocytomas, which are highly invasive, vascular neoplasms have an elevated expression of FGFs. The FGF family of mitogens have been implicated in the initiation and progression of astrocyte-derived tumors. It has been shown that human astrocytomas undergo parallel changes in FGF-receptor expression during their progression from a benign to a malignant phenotype. FGFR2 (bek) expression was abundant in normal white matter and in all low-grade astrocytomas but was not seen in malignant astrocytomas. Conversely, FGFR1 (flg) expression was absent or barely detectable in normal white matter but was significantly elevated in malignant astrocytomas. Thus differential expression of FGFRs may be critical in malignant progression of astrocytic tumors. Yamaguchi F., et al., 1994, Proc. Natl. Acad. Sci. 91: 484–488.

An established tumor model for the highly vascularized Kaposi's sarcoma secretes a species of the FGF family, Kaposi's sarcoma derived fibroblast growth factor (K-FGF). The K-FGF was found to induce a neoangiogenic response in nude mice bearing nontumorigenic human adrenal carcinoma transfectants. Pentosan polysulfate inhibited the K-FGF- induced growth. Wellstein et al., 1991, J. Natl. Cancer Inst. 83: 716–720.

Abnormalities in the FGF family signal transduction pathways have also been implicated in stomach cancer. The K-sam gene is homologous to the chicken bFGF receptor suggesting that the K-sam product is one of the receptors for the heparin-binding growth factor. The K-sam gene was expressed in several stomach cancer cell lines, a small cell lung cancer, and germ cell tumors. Hattori et al., 1990, Proc. Natl. Acad. Sci. 87: 5983–5987.

The int 2 gene, a site where integration of mouse mammary tumor virus frequently leads to cell transformation and the development of a tumor, encodes a protein that is homologous to the FGFs. Kasayama et al., 1993, J. Cell. Phy. 154: 254–261.

Many members of the FGF family are known to be powerful angiogenic factors. Heparin potentiates the mitogenic effect of aFGF on vascular endothelial cells and protects FGFs from inactivation. Other growth factors having an affinity for heparin, e.g., VEGF, are angiogenic endothelial mitogens. VEGF promotes the proliferation of endothelial cells. For this, cell surface associated heparin-like molecules are required for the binding of VEGF to its receptors.

Several heparin-like compounds have been used to treat cancers associated with heparin-binding growth factors and in particular, FGFs. Suramin seemed to work by inducing microagglutination of the growth factor but the clinical utility of Sumarin was limited because of side effects. Pentosan polysulfate inhibited the FGF-induced angiogenesis and tumor growth but because of its anticoagulant properties had toxicity problems. The present invention demonstrates that a sulfated saccharide salt or complex can act as an antagonist for heparin-induced oligomerization of occupied aFGF receptors and is even capable of antagonizing the effect of endogenous heparin-sulfates.

The FGFs have the ability to act as mitogens on a number of cell types, most prominently fibroblasts, endothelial cells, astrocytes, oligodendrocytes, neuroblasts, keratinocytes, bovine epithelial lens cells, asteoblasts and melanocytes. Thus proliferative activity of these cells in normal and diseased conditions can be modulated by FGF. Wagner J. A., 1991, Current Topics in Microb. Immun. 165: 95–118.

5.5.2 TREATMENT OF OTHER HEPARIN-BINDING GROWTH FACTOR-SENSITIVE DISORDERS

The Compounds and method of the invention can also be used to treat diseases or conditions associated with other heparin-binding growth factors or their receptors. VEGF, for example, has been associated with cancers such as glioma, Conn. et al, 1990, Proc. Natl. Acad. Sci. 87: 1323–1327, neuroblastoma, Levy et al, 1989, Growth Factors 2: 9–19, and autochthonous human lymphoma. Dvorak et al, 1991, J.Exp. Med. 174: 1275–1278. Amphoterin and heparin-binding growth factor-8 are both proteins involved in neurite outgrowth. Merenmies et al, 1991, J. Biol. Chem. 266: 16772–16729, and Li et al, 1990, Science 250: 1690–1694. Abnormal activity of these proteins could possibly be involved in various brain cancers. HB17 is a heparin-binding factor expressed in squamous cell and epidermoid carcinomas. Wu et al. 1991. J. Biol. Chem. 266: 16778–16785. and is thus implicated in cell proliferative diseases of the skin.

6. EXAMPLES: SYNTHESIS OF COMPOUNDS OF SPECIFIC FORMULAE

6.1 EXAMPLE I
Synthesis of calix(8)arene Octasulfate sodium

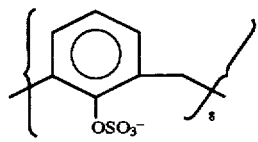

A solution of 100 mg of calix(8)arene in 3 ml of dimethylforamide and 1.0 g of sulfur trioxide pyridine complex was heated at 60° C. for 12 hrs. The reaction mixture was cooled at 0° C., quenched with 3 ml of methanol and stirred at room temperature (r.t.) for 2 hrs. The mixture was then evaporated to remove all the methanol and diluted with 5 ml of water and made basic with 1N sodium hydroxide solution to pH 10. This crude was eluted in P2 gel column with aqueous 0.2M ammonium acetate solution. The fractions containing the product were then combined and lyophilized. The solid was then dissolved in 5 ml of water and treated with ion exchange resin (AG 50W-X8 sodium). After removal of the resin by filtration, the solution was then lyophilized to provide 50 mg of Example I.

6.2 EXAMPLE II
Synthesis of Maltitol nonasulfate sodium

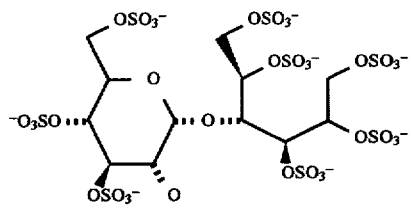

A solution of 100 mg of maltitol in a 5 ml solvent mixture of dimethylforamide (2.5 ml) and pyridine (2.5 ml) and 2.0 g of sulfur trioxide pyridine complex was heated at 100° C. for 18 hrs. The reaction mixture was cooled at 0° C. and quenched with 5 ml of methanol. Following the similar purification procedure. 45 mg of Example II was obtained.

6.3 EXAMPLE III
Synthesis of Maltotetrose tetradecasulfate sodium

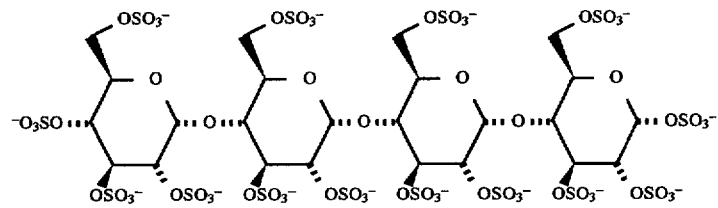

This compound was prepared as described in U.S. Pat. No. 3,788,910, issued Jan. 29, 1974.

6.4 EXAMPLE IV
Synthesis of 1(2,3,-trihydroxy)cyclopentyl-α-D-glucopyranoside heptasulfate sodium

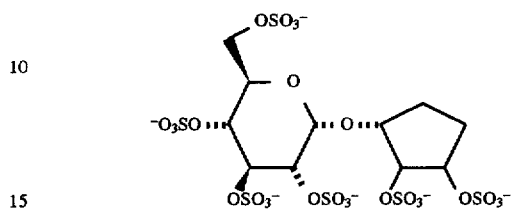

A solution of 600 mg of 1-bromo-2,3,4,6-tetra-O-benzyl-α-glucopyranose and 250 mg of cyclopentenol in a 5 ml solvent mixture of acetonitrile (2.5 ml) and dichloroethane (2.5 ml) was stirred with activated powdered 4 angstrom molecular sieves for 30 minutes. This was then cooled at −20° C., 350 mg of silver trifluorosulfonate was added to the mixture. The reaction flask was then sealed with aluminum foil and stirred at −20° C. overnight. The crude was then diluted with 50 ml of water and extracted with 2×50 ml of ethyl acetate. The combined organic extracts were washed with brine, dried (sodium sulfate), filtered and concentrated. The crude was then eluted on a silica gel column (hexane: ethyl acetate, 8:1) to provide 435 mg of the 1(2-cyclopentenly)-2,3,4,6-tetra-O-benzyl-α-D glucopyranoside.

To the above glycoside in a 10 ml solvent mixture of acetone (7 ml) and water (3 ml) was added 200 mg of N-methyl-morpholine N-oxide followed by 5 mg osmium tetraoxide. The mixture was then stirred at r.t. for 2 hrs, quenched with sodium thiosulfate solution and diluted with 30 ml of water. After extraction with 2×50 ml of ethyl acetate, the combined organic extracts were then washed, dried (sodium sulfate), filtered and concentrated. The crude was then eluted on a silica gel column (hexane: ethyl acetate, 1:2) to provide 400 mg of the 1(2,3-dihydroxylcyclopentyl) -2,3,4,6-tetra-O-benzyl-α-D-glucopyranoside.

The above glucoside was stirred with 400 mg of 10% palladium on carbon in 5 ml of methanol under 1 atm of hydrogen gas (balloon pressure) for 24 hours, filtered through celite which was washed with 30 ml of methanol. The combined filtrates were concentrated to give 150 mg of 1(2,3,-dihydroxylcyclopentyl)-α-D-glucopyranoside.

This glucoside was then sulfated as described in example I to provide 38 mg of 1(2,3,-trihydroxy)cylo-pentyl-α-D-glucopyranoside heptasulfate sodium.

6.5 EXAMPLE V

Synthesis of 1-Deoxy-1-[4-(1,2,3-trihydroxyl-n-butyl)-α-D-glucopyranoside heptasulfate.

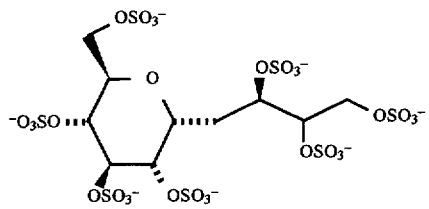

A solution of 10 grams of 1-deoxy-1-(3-propenyl)-2,3,4,6-tetra-O-benzyl-glucopyranose in a 30 ml solvent mixture of dichloromethane (15 ml) and methanol (15 ml) with 500 mg of sodium bicarbonate was bubbled with ozone until a blue color persisted. Excess ozone was removed by bubbling the mixture with argon. To the mixture was added 5 ml of dimethylsulfide. The mixture was stirred at r.t. for 12 hrs. and evaporated. The crude was dissolved in 300 ml of ethyl ether and washed with 100 ml of water. The organic layer was then washed with saturated bicarbonate, brine, dried (sodium sulfate), filtered and concentrated to provide 8 grams of 1-deoxy-1-(2-formymethyl)-2,3,4,6-tetra-O-benzyl-α-D-glucopyranose.

To a solution of 6 grams of the above compound in 50 ml of dichloromethane was added 4.5 grams of (methoxylcarbonylmethylene)triphenylphos phor-ane and the mixture was stirred at r.t. for 24 hours. After evaporation, the crude was suspended in 100 ml of ethyl acetate, filtered and evaporated with 300 ml of hexane. After removal of the triphenylphosphine oxide, the crude was purified on a silica gel column (hexane: ethyl acetate, 6:1) to produce 3.5 grams of E-1-deoxy-1-[3-(1-methoxylcarbonylpropenyl)-2,3,4,6-tetra-O-benzyl-α-D-glucopyranose.

A solution of 2.5 grams of above ester in 10 ml of dichloromethane at −78° C. was added with 10 ml of 1M diisobutylaluminum hydride in dichloromethane. The mixture was stirred at −78° C. for 2 hrs, quenched with 2 ml of methanol and warmed up to r.t. The mixture was then diluted with 200 ml of ethyl ether. 5 ml saturated sodium chloride solution was added and the mixture stirred at r.t. for 30 minutes. This was then dried with magnesium sulfate, filtered through celite and concentrated to produce 2.0 gram of E-1-deoxy-1-[4(1-hydroxy-2-butenyl)]-2,3,4,6-tetra-O-benzyl-α-D-glucopyranose.

Following the similar procedure as described in Example IV, the above compound (500) mg was dihydroxylated, debenzylated, sulfated and purified to provide 50 mg of Example V.

6.6 EXAMPLE VI

Synthesis of N(1-deoxy-α-1)-glucopyranocarboxyl]-L-serine-L-serine-L-serine heptasulfate sodium

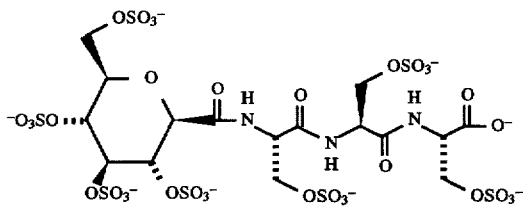

A solution of 5 grams of 1-deoxy-1-hydroxymethyl-2,3,4,6-tetra-O-acetyl-β-D-glucopyranose, prepared according to published procedure, Chatani, N.; Ikeda, T.; Sonoda, N.; Kurosawa, H.; Kawasaki, Y.; Murai, S., 1988, J. Org. Chem. 53; 3387, in 10 ml of acetone at 0° C. was added to Jones reagent and stirred at r.t. for 2 hours. The mixture as then concentrated and diluted with water followed by extraction with 2×100 ml of ethyl acetate. The combined organic extracts were then washed with water followed by brine, and then dried, filtered and concentrated to produce 4.1 grams of 1-deoxy-1-carboxyl-2,3,4,6-tetra-O-acetyl-β-D-glucopyranose.

A solution of 4.0 grams of the above acid in 30 ml of dichloromethane was added with 1.3 grams of N-hydroxysuccimide followed by 2.2 grams of 1,3-dicyclohexylcarbodimide. The mixture was then stirred at r.t. overnight, filtered and the filtrate concentrated. The crude was then crystallized from ethyl acetate and hexane to produce 4.6 grams of the activated ester.

A solution of 1.0 grams of above ester in 5 ml of dimethylforamide was added with 800 mg of tris-O-butyl-Ser-Ser-Ser methyl ester and stirred at r.t. overnight. The mixture was then diluted with 100 ml of dichloromethane, washed with 30 ml of water followed by brine, and then dried with sodium sulfate, filtered and concentrated. The crude was then purified on a silica gel column with 10% methanol in chloroform to provide 1.2 grams of the C-glycopeptide.

The above material was then stirred with 3 ml each of dichloromethane and trifluoroacetic acid for 6 hrs and all the volatiles were removed in rotavaporator. The crude was then hydrolysed with catalytic amount of sodium methoxide and methanol followed by base hydrolysis (1N sodium hydroxide/methanol/water). The resulting C-glycopeptide was then sulfated and purified as described in Example I to provide Example VI.

6.7 EXAMPLE VII

Synthesis of 1-deoxy-1-n-propyl maltose heptasulfate sodium.

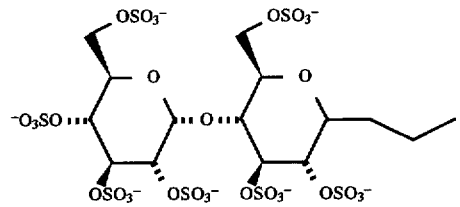

To a solution of 2 grams of maltose octaacetate in 5 ml of acetonitrile and powdered molecular sieves at r.t., was added 2 ml of allyltrimethylsilane followed by 1 ml of boron trifloride etherate. The mixture was stirred at r.t. overnight, quenched with 50 ml of water and extracted with 2×50 ml of ethyl acetate. The combined organic extracts were washed with saturated sodium bicarbonate, followed by brine, and then dried with sodium sulfate, filtered and concentrated. The crude was then purified on a silica gel column (hexane: ethyl acetate, 1:1) to provide 800 mg of 1-deoxy-1-(3-propenyl) maltose heptaacetate.

The above crude was hydrogenated in methanol with 5% palladium on carbon to provide 780 mg of the propyl maltose heptaacetate.

To the above acetate in dry methanol was added a small piece of sodium metal and stirred at r.t. overnight. The mixture was acidified with cation exchange resin (Dowex 50 W) to provide 200 mg of the 1-deoxy-1-propylmaltose.

The above material was then sulfated and purified as described in Example I.

6.8 EXAMPLE VIII
Synthesis of 1-deoxyl maltose heptasulfate sodium

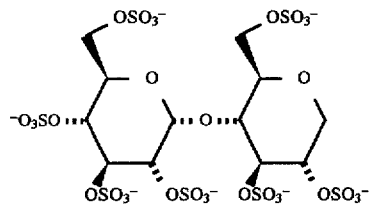

A solution of 3 grams of acetobromo maltose heptaacetate in 20 ml of toluene and 1.5 ml of tributyltin hydride with 200 mg of azoisobutyronitrile was heated at 120° C. for 3 hours. All the toluene was removed in a rotavaporator and the mixture diluted with 300 ml of ethyl acetate, washed with saturated 3% ammonium hydroxide solution, followed by brine, and then dried with sodium sulfate, filtered and concentrated. The crude was then purified on a silica gel column (hexane: ethyl acetate, 3:1) to provide 900 mg of 1-deoxy maltose hepatacetate.

This material was then saponified with catalytic sodium methoxide in methanol as described in Example VII, sulfated and purified as described in Example I to provide 80 mg of 1-deoxy maltose heptasulfate sodium.

6.9 EXAMPLE IX
Synthesis of N-acetyl-1-deoxy-1-n-octylamino maltose hepatsulfate

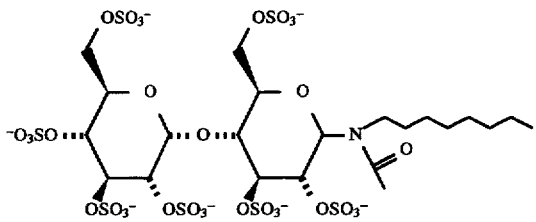

A solution of 3 grams of maltose in a solvent mixture of ethanol (5 ml) and octylamine (3 ml) was heated at 80° C. overnight. After removal of all the volatile solvent in high vacuum, the amino glycoside in 10 ml of ethanol was stirred with 1.0 ml each of acetic anhydride overnight and evaporated to dryness. The crude amide was then crystallized from methanol to provide 900 mg of N-acetyl-1-deoxy-1-n-octylamino maltose.

The above material (200 mg) was then sulfated and purified as described in Example I to provide 60 mg of Example IX.

6.10 EXAMPLE X
Synthesis of 2-deoxy-2-[4(2,3,4-trihydroxyl)n-butyl)-α,-D-fructofuranose heptasulfate.

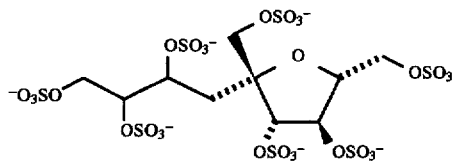

2-deoxy-2-(3-propenyl)-1,3,4,6-tetra-O-benzyl-β-D-fructofuranose was prepared according to the published procedure, Nicotra, F., Panza, L., Russo, G. J., 1988, Org. Chem. 52: 5627, was ozonized, extended, reduced, hydrogenated, sulfated and purified as described in Example V.

6.11 EXAMPLE XI
Synthesis of 1-deoxy-1-hydroxymethyl-maltose octasulfate sodium

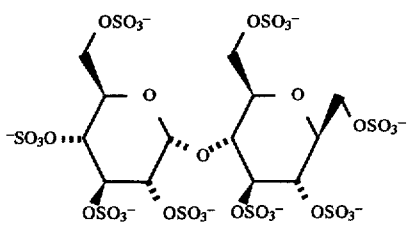

A solution of 2.0 grams of maltose octasulfate in 20 ml of dichloromethane was stirred with 2.0 ml of diethylmethyl silane and 200 mg of dicobatt octacarbonyl at r.t. for 2 days. All volatiles were evaporated. The residue was then stirred in 10 ml of methanol with catalytic amount of sodium methoxide. This material, 1-deoxy-1-hydroxymethyl-maltose was then worked-up as described in Example VII, and purified as described in Example I.

7. EXAMPLES: ASSOCIATION OF aFGF WITH FGFR2 AND INFLUENCE OF HEPARIN ON THIS INTERACTION

To study the association of aFGF with FGFR2 (bek) in vitro, and the influence of heparin upon this interaction, a system free from any other potentially interacting cell-surface components was required. Therefore, large quantities of the soluble extracellular domain of FGFR2 (sFGFR) were generated by expression in CHO cells or insect cells, and of aFGF by expression in E. coli. Chemical cross-linking studies, isothermal titration calorimetry, and non-denaturing gel-electrophoresis were then employed to investigate the interactions and their effects upon receptor oligomerization state.

7.1. MATERIALS AND METHODS

Heparin (16 kDa), was purchased from Sigma, and heparin (5 kDa) was from Calbiochem. Endoglycosidase F (N-glycosidase F-free) was purchased from Boehringer Mannheim Inc. Disuccinimidyl suberate (DSS) and bis (sulfosuccinimidyl) suberate ($BS^3$) were purchased from Pierce. Rabbit polyclonal anti-phosphotyrosine (anti-P-Tyr) antibodies were generated in our laboratory. Anti-FGFR2 (anti-bek 1A) polyclonal antibodies directed against the C-terminal peptide of FGFR2 (Dionne et al., 1990) were used for immunoprecipitation. Anti-FGFR2 (EC1 and 78) polyclonal antibodies directed against the extracellular domain of FGFR2 were used for immunoblotting. Polyclonal anti-aFGF antibodies generated against aFGF purified from E. coli were prepared in our laboratory. aFGF was expressed in E. coli and purified as described (Jaye et al., 1987, J. Biol. Chem. 262, 16612–16617) by binding to a heparin-sepharose (Pharmacia) column and eluting in high salt buffer (50 mM Tris pH 7.5, 1.5M NaCl) (Jaye et al., 1987).

7.1.1. GENERATION OF sFGFR CONSTRUCT

A plasmid encoding the extracellular, ligand-binding domain of human FGFR2 (residues 1–355) was constructed using standard oligonucleotide-directed mutagenesis (Amersham) to introduce a translational termination codon immediately prior to the beginning of the single transmembrane domain of the receptor (Dionne et al., 1990). BamHI and SacII restriction sites were introduced 3' to the new termination codon. An XbaI-SacII fragment was isolated from the replicative form (RF) of this M13 mutagenesis product, filled in using T4 DNA polymerase (Boehringer-Mannheim) and inserted into the SmaI site of the expression vector pCVN (Dionne et al., 1990). This expression vector, which contains both the neomycin resistance and the dihydrofolate reductase genes for selection and amplification, was transfected into CHO cells following published procedures. Wigler et al., 1979, Cell 16:777–785.

For expression directed by recombinant baculoviruses, a fragment containing the extracellular portion of FGFR2 was subcloned via a blunt-end ligation into the BglII site of the BlueBacIII baculovirus transfer vector (Invitrogen). The sequence of the insert was verified by DNA sequence analysis (U.S. Biochemicals). The recombinant baculovirus plasmid was co-transfected with BaculoGold DNA into Sf9 insect cells as described by the manufacturer (Pharmigen). Blue plaques in the plaque assay were analyzed for the production of recombinant protein. Positive recombinant virus stock was amplified and used for protein production. HighFive cells (Invitrogen) were seeded in roller bottles and were then infected with a high-titer stock suspension of the recombinant baculovirus ($\sim$1–3×10$^8$ virus particles/ml) after 24 hours. Optimal levels of protein production were achieved when the MOI was between 5 and 10. Medium was collected 62 hours after virus infection.

7.1.2. PURIFICATION OF sFGFR sFGFR was purified from the conditioned medium of CHO cells or Sf9 cells secreting the protein in three steps. The first step was affinity chromatography using a heparin-sepharose column (Pharmacia LKB Biotechnology) pre-saturated with aFGF. The column was washed extensively with 0.01M phosphate buffer, pH 7.4 containing 0.5M NaCl. The sFGFR was eluted from the heparin column together with the ligand in 0.01M phosphate buffer pH 7.4 containing 1M NaCl. The eluted fractions were analyzed by 15% SDS-PAGE gel, and fractions containing aFGF and sFGFR were concentrated using an Amicon stir-cell (350 ml) and an Amicon 76 YM30 membrane. In the second step, the concentrated material was applied to a Superose 12 size-exclusion column in 0.01M phosphate buffer, pH 7.4, containing 0.5M NaCl, in order to separate the occupied sFGFR from unbound aFGF. Fractions were analyzed on a 15% SDS-PAGE gel, and those containing occupied sFGFR were pooled for further purification. The pooled fractions were applied to a lentil lectin Sepharose 4B column (Sigma), pre-equilibrated with 0.01M phosphate buffer, pH 7.4, containing 0.5M NaCl. The column was washed extensively using the same buffer and the sFGFR was eluted using 10% methyl-α-D-mannopyranoside (Sigma) in 25 mM HEPES, pH 7.5, 150 mM NaCl. Fractions containing purified sFGFR were pooled and concentrated using a Centricon 30 (Amicon). The purified sFGFR was stored in 25 mM Hepes, pH 7.5, 150 mM NaCl, at 4° C. CHO cell-conditioned medium yielded 0.5–1 mg/liter of sFGFR, while Sf9 cells produced approximately 7 mg of sFGFR per liter of conditioned medium.

7.1.3 COVALENT CROSS LINKING EXPERIMENTS

Cross linking of the soluble receptor

Purified sFGFR (0.2 μM) was incubated with aFGF (0.6 μM) in the presence or absence of heparin. The mixture was incubated in 25 mM HEPES, pH 7.5, 150 mM NaCl (final volume 40 μl) for 1 hour at room temperature. The covalent cross linking agent disuccinimidyl suberate (DSS) was added to a final concentration of 0.25 mM. After 20 min of incubation, the reaction was quenched by the addition of 50 mM Tris-HCl and 100 mM glycine for 10 min. Samples were then mixed with SDS-PAGE sample buffer and boiled for 5 min. The samples were separated on a 6–12% gradient SDS-PAGE gel, transferred to nitrocellulose membranes, and immunoblotted with either polyclonal anti-FGFR2 (EC1 and 78) or anti-aFGF antibodies. The blots were incubated with $^{125}$I-protein A and autoradiographed. Cross-linking studies of aFGF alone were performed using the same procedure, except that samples were analyzed by 15% SDS-PAGE and detected by staining with Coomassie Brilliant Blue.

Cross-linking studies of FGF receptors in CHO cells

Cells grown in fibronectin-coated dishes were starved overnight in F-12 medium containing 0.5% FBS. Cells were then washed with ice-cold binding medium (F-12 medium containing 20 mM Hepes (pH 7.5) and 0.1% BSA), and incubated for 1 hour at 4° C. with either aFGF (0.1 nM), heparin (50 nM), or both. The cells were then washed twice with cold PBS and incubated with 1 mM BS$^3$ in PBS for 20 minutes at room temperature. The cross-linking reaction was quenched by the addition of 50 mM Tris-HCl and 100 mM glycine for 10 min at room temperature. The cells were then washed with cold PBS and lysed in lysis buffer (20 mM HEPES, 150 mM NaCl, 10% glycerol, 1% Triton X-100, 1.5 mM MgCl$_2$, 1.5 mM EGTA, 1 μM aprotinin, 1 μM leupeptin, 1 mM phenylmethylsulphonyl fluoride, 200 μM sodium ortho-vanadate). FGFR was then immunoprecipitated from cell lysates with anti-FGFR2 antibodies, separated by SDS-PAGE (6–8% gradient gel), transferred to a nitrocellulose membrane and immunoblotted with anti-FGFR2 antibodies.

7.1.4 ANALYSIS OF aFGF/sFGFR/HEPARIN COMPLEX FORMATION BY NON-DENATURING PAGE aFGF alone, or a pre-incubated mixture of heparin and aFGF (molar ratio 1:10) was added to a solution containing sFGFR. The mixtures were then incubated for 20 min at room temperature in 20 mM Hepes pH 7.5, 200 mM NaCl. Size-exclusion chromatography, using a Superose 12 column (Pharmacia), was then employed to separate free aFGF and sFGFR from the complex that formed. Fractions containing the isolated complexes were pooled, and analyzed by non-denaturing PAGE (4–15% gradient gels), using the Phastsystem (Pharmacia). Gels were stained with Coomassie Blue. In the case of the sFGFR/heparin mixture (FIG. 4, lane 2), heparin was simply added to the sFGFR solution prior to electrophoresis.

7.1.5. GENERATION OF CELL LINES EXPRESSING FULL-SIZE FGFR

Wild-type CHO cells (CHO-K1), as well as heparin sulfate-deficient mutant cells (CHO-pgsD-677) which were kindly provided by Prof. J. Esko (Esko, 1991), were cultured in F-12 medium containing 7.5% FBS, 1% Ampicillin/Streptomycin and 1% glutamine. Both CHO cell lines were co-transfected with the wild-type human FGFR2 (bek) DNA in the expression vector pMJ30 (Dionne et al., 1990) (40 μg/10 cm dish) and the pSVneo resistant gene (0.5 mg/10 cm dish), using the calcium phosphate method (Chen and Okayama, 1987). Geneticin (1 mg/ml) resistant clones were screened for expression of the receptor by immunoprecipitation and immunoblotting analysis using anti-FGFR2 antibodies.

7.1.6 TYROSINE PHOSPHORYLATION OF THE bek FGFR IN CHO CELLS

Wild-type and mutant CHO cells were starved overnight in F-12 medium containing 0.5% FBS, and stimulated with either 0.1 nM aFGF, 50 nM heparin, or both, for 5 min at 37° C. Cells were lysed, immunoprecipitated with anti-FGFR2 antibodies and analyzed by immunoblotting with anti-phosphotyrosine (anti-PTyr) antibodies.

7.2. RESULTS

7.2.1. PURIFICATION OF THE SOLUBLE EXTRACELLULAR DOMAIN OF FGFR2 (sFGFR)

Vectors capable of directing the synthesis of the soluble extracellular domain (residues 1–355) of FGFR2 (sFGFR) in CHO or Sf9 cells were generated as described in Materials and Methods. Cells transfected with the appropriate vector secreted sFGFR, which was then purified from their conditioned medium by affinity chromatography using columns on which aFGF and lectin respectively had been immobilized. The purified sFGFR migrated in SDS-PAGE with an apparent molecular weight of approximately 65 kDa (FIG. 2). After treatment with endoglycosidase F, sFGFR migrated as a 46 kDa protein consistent with the predicted molecular mass of the core protein (Dionne et al., 1990). This demonstrates that glycosylation of at least some of the 8 potential N-linked glycosylation sites in sFGFR occurs. Similar treatment with endoglycosidase F of living cells causes a reduction in the apparent molecular weight of full-length FGFR2 from 135 kDa to approximately 90 kDa (Dionne et al., 1990).

7.2.2. BINDING OF aFGF TO sFGFR

The binding of aFGF to sFGFR was studied using the technique of isothermal titration calorimetry (ITC). In this technique the heat liberated (or absorbed) upon binding is monitored as small aliquots of ligand are added sequentially to a solution of the receptor at known concentration, which is maintained at constant temperature. A binding curve is thus generated, and fitting of this to the equation for the binding reaction gives values for the binding constant, stoichiometry, and enthalpy (Wiseman et al., 1989). The stoichiometry of aFGF binding to sFGFR in the absence of added heparin was determined to be 0.9±0.14, and $K_D$ was determined to be 528±173 nM (Table 1). The thermodynamics of this interaction are considered in more detail elsewhere. The binding observed in these studies is somewhat weaker than that reported for the binding of aFGF to intact FGFR present in cell membranes (Dionne et al., 1990; Ornitz et al., 1992). A similar discrepancy has been observed when the EGF binding affinity of intact EGFR and its soluble extracellular domain are compared (Zhou et al. 1993; Lax et al. 1991; Hurwitz et al. 1991), as well as in the case of human growth hormone binding to its receptor (Fuh et al., 1992). There are several likely reasons for this discrepancy. It could, for example, arise from avidity effects that operate at the cell-surface when the receptor is restricted to diffusion in just two dimensions, but not when both components are free in solution. Additionally, in the case of measurements of aFGF binding to its receptor in whole cells, the effective concentration of the growth factor at the cell surface is likely to be increased significantly as a consequence of its interaction with cell-surface HSPG molecules. Thus, the local concentration of aFGF experienced by the receptor will be greater than that assumed in the binding study. This will lead to an overestimate of the affinity, which is the most likely reason for the discrepancy in this case.

When aFGF binding to sFGFR was studied in the presence of heparin, by titrating sFGFR into a mixture of heparin and aFGF, no effect upon the binding parameters could be detected. This is in contrast to other studies, which indicate that the presence of heparin is required for the bFGF/FGFR interaction (Rapraeger et al., 1991, Yayon et al., 1991, Ornitz et al., 1992). However, it has also been reported that heparin is not required for the binding of bFGF to the soluble extracellular domain of FGFR1, or to full length FGFR1 and 2 expressed in mutant cells lacking HSPG molecules at the cell-surface (Roghani et al., 1994).

Analysis of heparin binding to sFGFR by ITC failed to detect an interaction with significant affinity. Furthermore, binding of sFGFR to a heparin-sepharose column could not be detected. These data support the conclusion that heparin does not interact strongly with sFGFR2, contrary to recent reports that heparin binds to the extracellular domain of FGFR1 (Kan et al., 1993).

7.2.3. ACIDIC FGF ALONE DOES NOT PROMOTE sFGFR DIMERIZATION

Previous studies of the soluble extracellular domains of the EGFR (Lax et al. 1991) and c-kit (Lev et al. 1992) showed that binding of the cognate ligand resulted in dimerization of the soluble receptor. If aFGF activates its receptor in a similar manner, aFGF binding to sFGFR would therefore be expected to promote its dimerization. To test this, sFGFR was treated with the covalent cross-linking reagent disuccinimidyl suberate (DSS), both in the presence and the absence of aFGF. Samples were then analyzed by SDS-PAGE, followed by immunoblotting with either anti-FGFR2 or anti-aFGF antibodies. FIG. 3 (lanes 3 and 7) shows that sFGFR migrated as a mixture of 65 and 80 kDa species after cross-linking in the presence of aFGF alone. The 65 kDa form corresponds to free sFGFR, while the 80 kDa form corresponds to sFGFR to which the 15 kDa aFGF has been cross-linked. No cross-linked dimeric form of sFGFR could be detected, by contrast with what has been reported for the other receptors. Thus, although aFGF binds to sFGFR, it does not induce its dimerization.

7.2.4. aFGF AND HEPARIN TOGETHER INDUCE sFGFR DIMERIZATION

Since heparin-like molecules have been reported to be necessary for biological responses to FGF binding (Rapraeger et al., 1991, Yayon et al., 1991, Ornitz et al., 1992), chemical cross-linking studies were performed in which both heparin and aFGF were added to sFGFR. FIG. 3 (lanes 4 and 8) shows that cross-linked dimers of sFGFR are formed under these conditions, whereas they were not detected in the presence of aFGF alone. In addition to the 65 kDa and 80 kDa bands observed when an sFGFR/aFGF mixture was treated with DSS, an additional band appears when an sFGFR/aFGF/heparin mixture is treated. This band corresponds to a species of approximately 160 kDa, consistent with it representing a complex of two sFGFR plus two aFGF molecules. The addition of heparin alone to sFGFR followed by treatment with DSS did not affect the mobility of sFGFR (FIG. 3, lane 2). Heparin itself does not bind to sFGFR, but has been reported to bind to aFGF with relatively high affinity, in a multivalent fashion (Mach et al., 1993). These data support a model in which aFGF/heparin complex may act as a multivalent ligand for FGFR. By analogy with the PDGF dimer (Heldin et al. 1988; 1989), binding of each ligand molecule in the complex to its cognate receptor could bring receptor molecules together, and lead to their dimerization.

7.2.5. HEPARIN BINDING CAUSES aFGF OLIGOMERIZATION

In further support of the model proposed herein, ITC studies showed that aFGF binds to heparin molecules of two different average molecular weights (16 kDa and 5 kDa) with high stoichiometries. The data are presented in Table I.

TABLE I

Isothermal Titration Calorimetry Data for aFGF Binding to sFGFR and Heparin Fragments

| Reaction | Stoichiometry n[1] | $K_D$ (nM)[2] | ΔH (kcal mol$^{-1}$) |
|---|---|---|---|
| aFGF binding to sFGFR | 0.90 ± 0.14 | 528 ± 173 | −5.3 ± 2.0 |
| aFGF binding to 4.8 kDa heparin | 3.94 ± 0.27 | 461 ± 357 | −4.8 ± 0.7 |
| aFGF binding to 16 kDa heparin | 11.1 ± 0.28 | 505 ± 227 | −5.1 ± 0.28 |
| aFGF binding to sucrose octasulfate | 0.91 ± 0.29 | 3397 ± 1344 | −5.8 ± 1.2 |

Values quoted are the means for two experiments in the case of aFGF binding to the heparins, and three in the case of aFGF binding to sFGFR. Values for standard deviation are also given.
[1]All values for stoichiometry refer to aFGF as the ligand molecule.
[2]Fits to the binding isotherms obtained by titration calorimetry assume a single class of binding sites.

The $K_D$ for aFGF binding to 16 kDa heparin was 505 nM, with a stoichiometry of 11:1 (aFGF:heparin). $K_D$ for aFGF binding to 5 kDa heparin was similar (461 nM), and the stoichiometry was 4:1. Thus one aFGF binds per approximately 4–5 saccharide units of heparin. Similar results have recently been reported from studies involving light scattering, ultracentrifugation, and surface plasmon resonance (SPR) (Mach et al., 1993).

These values for the stoichiometry of aFGF binding to heparin indicate that the interaction results in aFGF oligomerization, as has been reported for bFGF (Ornitz et al., 1992). This was tested in chemical cross-linking experiments. aFGF was treated with DSS in the presence and absence of heparin (16 kDa), and the reaction mixture was analyzed on a 15% SDS gel under reducing conditions (FIG. 4A). In the absence of heparin, aFGF migrates with an apparent molecular weight of approximately 16 kDa, and is unaffected by DSS treatment (FIG. 4A, lanes 1 and 2). However, in the presence of heparin, an additional band, corresponding to a species of approximately 32 kDa, appears in a DSS-dependent fashion, together with bands of higher molecular weight (FIG. 4A, lane 4). These bands represent dimers of aFGF, as well as higher order oligomers. SDS-PAGE under non-reducing conditions confirmed that disulfide-bond formation was not responsible for the oligomerization (FIG. 4B). Similar results have also recently been reported for bFGF (Ornitz et al., 1992). These data support the conclusion that heparin is indeed able to induce the oligomerization of both aFGF and bFGF, and that this is likely to provide the driving force for receptor oligomerization when an FGF/heparin complex binds to FGFR.

7.2.6 ANALYSIS OF aFGF/sFGFR/HEPARIN COMPLEX FORMATION BY NON-DENATURING PAGE

The requirement of both heparin and aFGF for the induction of sFGFR dimerization was also confirmed in a second experimental system. sFGFR was incubated with aFGF alone, or with aFGF plus heparin. The complexes that formed were separated from their free components by size-exclusion chromatography, and analyzed by non-denaturing PAGE. sFGFR has high mobility in this gel system (FIG. 5, lane 1), which is reduced slightly upon complex formation with aFGF (FIG. 5, lane 3). Addition of heparin alone had no significant effect upon the migration of sFGFR (FIG. 5, lane 2), whereas when aFGF and heparin (16 kDa) were both added to sFGFR, the tertiary complex showed significantly reduced mobility (FIG. 4, lane 4). In addition, there was an increase in the apparent heterogeneity, indicating that several different oligomerization states of the complex may occur.

7.2.7 EFFECTS OF HEPARIN UPON aFGF-INDUCED FGFR DIMERIZATION AND AUTOPHOSPHORYLATION IN CHO CELLS

Based upon the in vitro studies described above, it was concluded that the role of heparin is to induce the oligomerization of aFGF, which can then bind to the receptor in a multivalent manner, resulting in its dimerization and consequent activation. This situation is similar to the induction of PDGF-receptor dimerization upon binding of the dimeric PDGF ligand (Heldin et al., 1988; 1989). In order to determine the relevance of this model in the context of living cells, the effect of heparin upon aFGF-induced activation of full-length FGFR2 was studied, both in cells that do and cells that do not express HSPG molecules on their cell-surface.

Full-length FGFR2 was transfected into two CHO cell lines; wild-type CHO-K1, and the mutant CHO-pgsD-677, which is defective in heparin sulfate expression at its cell-surface (Esko, 1991). Cells were stimulated with aFGF in the presence or absence of added heparin, and incubated with the covalent cross-linking agent, BS[3]. Cells were then lysed, and immunoprecipitated FGFR2 was analyzed by SDS-PAGE followed by immunoblotting with anti-FGFR2 antibodies. As shown in FIG. 6 (lanes 3 and 4), aFGF could induce receptor dimerization regardless of the presence of exogenous heparin in the case of CHO-K1 cells. However, when the CHO-pgsD-677 mutants were analyzed, aFGF could only induce the dimerization of FGFR2 when exogenous heparin was added (FIG. 6, lanes 7 and 8). Moreover, FIG. 7 (lanes 1–4) shows that receptor autophosphorylation correlated with our ability to detect covalently cross-linked dimers in this study. Thus in wild-type CHO-K1 cells, addition of aFGF alone resulted in the stimulation of FGFR2 autophosphorylation (FIG. 7, upper panel, lane 3), whereas exogenously supplied heparin was required for significant levels of aFGF-induced FGFR2 autophosphorylation in the heparin-deficient CHO cells (FIG. 7, lower panel, lanes 3 and 4). Identical results were also obtained when FGFR1 (flg) was expressed in the two different CHO cell-lines. Therefore, taken together, these data strongly support the assertion that heparin-like molecules are required for the induction of receptor dimerization upon binding of FGF in vivo.

7.2.8 SYNTHETIC HEPARIN ANALOGS CAN PREVENT aFGF-INDUCED RECEPTOR DIMERIZATION AND ACTIVATION

Based upon the model presented herein (FIG. 1A), it was predicted that the presence of heparin analogs that bind to aFGF in a monovalent manner should inhibit the ability of aFGF to induce receptor dimerization and activation. Calorimetric studies of aFGF binding to heparin and various synthetic analogs (Table 1) showed that the synthetic analog, sucrose octasulfate, binds to aFGF in a 1:1 complex, with a $K_D$ of 3.4 µM. Crystallographic studies of an aFGF/sucrose octasulfate complex have also shown a 1:1 stoichiometry (Zhu et al., 1993).

aFGF can only induce FGFR dimerization in the presence of heparin (FIG. 6, lane 8). The interaction of a single molecule of heparin with several aFGF molecules is required for this effect (FIG. 4A, lane 4). In addition, in cells that do not express HSPG molecules at their surface, the addition of heparin is required for aFGF to activate FGFR (FIG. 7, lane 4). Sucrose octasulfate binds to only a single molecule of aFGF. Indeed, addition of sucrose octasulfate does not enable aFGF to activate FGFR in the mutant (HSPG-deficient) CHO cells (FIG. 7, lane 6). Moreover, the addition of an excess of sucrose octasulfate to a mixture of aFGF and heparin that is ordinarily able to activate the receptor was inhibitory (FIG. 7, lanes 4, 7, 8). This effect was seen both in the mutant CHO cells as well as in CHO cells that express HSPG's at their surface. Thus, sucrose octasulfate can act as an antagonist for heparin-induced oligomerization of occupied aFGF receptors, and is even capable of antagonizing the effect of endogenous heparin-sulfates (FIG. 1B).

The present invention is not to be limited in scope by the specific embodiments described which are intended as single illustrations of individual aspects of the invention, and functionally equivalent methods and components are within the scope of the invention, in addition to those shown and described herein will become apparent to those skilled in the art from the foregoing description and accompanying drawings. Such modifications are intended to fall within the scope of the appended claims.

What is claimed is:

1. A method for treating a cancer or angiogenic abnormality involving abnormal cell proliferation induced by the binding of an oligomerized heparin growth factor ligand-heparin complex to its receptor, which comprises administering to a patient in need of such treatment an amount of sucrose octasulfate effective to prevent oligomerization of heparin growth factor, wherein said amount is in excess of that sufficient to activate said receptor.

2. The method of claim 1 in which sucrose octasulfate is in the form of a salt of an alkali metal or alkaline earth metal.

3. The method of claim 2 in which the salt is a sodium, potassium, bismuth, calcium, magnesium, barium, aluminum, zinc, copper, titanium, or manganese salt.

4. The method of claim 1 in which sucrose octasulfate is in the form of a salt of an organic base.

5. The method of claim 1 in which the cancer is selected from the group consisting of stomach cancer, brain cancer, Kaposi's sarcoma, small cell lung carcinoma, and mammary tumor.

6. The method of claim 1, wherein the cancer or angiogenic abnormality is selected from the group consisting of nasopharyngeal angiofibroma, proliferative retinopathy, and intraocular neovascularization.

7. The method of claim 3, in which the salt is potassium sucrose octasulfate.

8. The method of claim 3, in which the salt is sucralfate.

9. The method of claim 1, wherein the sucrose octasulfate is administered orally, rectally, vaginally, transmucosally, via intestinal administration, intramuscularly, subcutaneously, via intramedullary injections, intrathecally, intraventricularly, intravenously, intraperitoneally, intranasally, or via intraocular injection.

* * * * *